United States Patent
Lin

(10) Patent No.: US 8,138,936 B2
(45) Date of Patent: Mar. 20, 2012

(54) METHOD FOR TESTING PERSONNEL ESD GROUNDING DEVICES WITH FUNCTION OF NEAR-FAIL ALERT AND DEVICE FOR PERFORMING THE SAME

(76) Inventor: Tony-Sheng Lin, Taipei County (TW)

( * ) Notice: Subject to any disclaimer, the term of this patent is extended or adjusted under 35 U.S.C. 154(b) by 437 days.

(21) Appl. No.: 12/178,589

(22) Filed: Jul. 23, 2008

(65) Prior Publication Data

US 2010/0019914 A1     Jan. 28, 2010

(51) Int. Cl.
*G08B 21/00* (2006.01)

(52) U.S. Cl. ........ 340/649; 340/540; 340/635; 702/183; 702/182; 702/184; 702/185; 702/188

(58) Field of Classification Search .................. 340/649, 340/540, 635; 324/500, 557, 509, 510; 702/183, 702/182, 184, 185, 188
See application file for complete search history.

(56) References Cited

U.S. PATENT DOCUMENTS

| | | | | |
|---|---|---|---|---|
| 4,710,751 A | * | 12/1987 | Webster | 340/522 |
| 5,835,327 A | * | 11/1998 | Siew et al. | 361/111 |
| 5,872,455 A | * | 2/1999 | Pohribnij et al. | 324/509 |
| 6,108,614 A | * | 8/2000 | Lincoln et al. | 702/183 |
| 6,205,408 B1 | * | 3/2001 | Jubin et al. | 702/182 |
| 6,809,522 B2 | * | 10/2004 | Nguyen | 324/457 |
| 2002/0089805 A1 | * | 7/2002 | Maritz et al. | 361/224 |
| 2003/0234651 A1 | * | 12/2003 | Nguyen | 324/500 |
| 2008/0143314 A1 | * | 6/2008 | Li | 324/76.11 |
| 2009/0210210 A1 | * | 8/2009 | Imtiaz | 703/14 |

* cited by examiner

*Primary Examiner* — Hoi Lau

(57) ABSTRACT

A method for testing personnel ESD grounding devices with a function of near-fail alert is disclosed. A near-fail range is set. When the measurement of the resistance for a wrist strap or a footwear is within the near-fail range; an alarm is actuated to alert the user that the static electricity prevention device worn by the user will fail soon. The near-fail range is provided so that the user can receive an alert when the wrist strap or the footwear being worn on will fail soon in the near future and thus to remind the user to adopt proper reactions to change or fix the personnel ESD grounding device to prevent its sudden failure during actual use. Furthermore, the test provides digital readouts and has higher precision to avoid faulty results. Moreover, the wrist strap and footwear are tested simultaneously and individual results can be derived so as to avoid errors in test. A device for performing the method is also provided.

3 Claims, 6 Drawing Sheets

METHOD FOR TESTING PERSONNEL ESD GROUNDING DEVICES WITH FUNCTION OF NEAR-FAIL ALERT AND DEVICE FOR PERFORMING THE SAME

FIELD OF THE INVENTION

The present invention relates to control of electro-static discharge (ESD) and safety; and particularly to a method for testing personnel ESD grounding devices with a function of near-fail alert and a device for performing the same; in that a near-fail range is provided so that the user can receive an alert when the wrist strap or footwear worn on will fail soon in the near future and thus the user is reminded to take proper actions to change or fix the personnel ESD grounding device to prevent sudden failure of the devices during actual use. Furthermore, the test provides digital readouts and has higher precision to avoid faulty results. Moreover, the wrist strap and the footwear are tested simultaneously and individual results can be derived so as to avoid errors in test.

BACKGROUND OF THE INVENTION

Today, the personnel ESD testing has become a mandatory requirement in ESD-Protected Areas (EPA). In many EPA areas, the testing and recording of ESD footwear and wrist-strap is manually conducted in "fuzzy" traditional ways. One most popular traditional way is to use a tester with a high resistance limit and a low resistance limit. When the wrist-strap or footwear under test has a resistance above the high limit, a high-fail LED will turn on. When the measured resistance is between the high and low limits, a pass LED will turn on. When the measured resistance is below the low limit, a low-fail LED will turn on. The measured result is fuzzy because it did not calculate and display the actual resistance being measured. Such "fuzzy" testing has created many issues in the fields that implemented an ESD-Control program. One of the major issues is the low accountability of the test results.

Conventionally, to test the normal functionality of a wrist strap or a footwear, simple traditional testing devices as described in the above paragraph are used. The traditional testing is to find out at testing time whether the device-under-test (DUT) is good or bad. If the ESD grounding device is found to be bad, then it will be discarded and replaced by a good one. In many applications, this replacement action turns out to be a bit too late since many of the ESD-sensitive (ESDS) products could have been damaged by the operators working on them wearing failed ESD grounding devices. Such situation is particularly critical in highly ESD sensitive areas such as aerospace electronics assembly plants or military-related production lines. A more desirable way of handling such cases is to identify the "About-To-Fail" (ATF) grounding devices and avoid using them when work in the EPA. Using such a well-managed scheme, we can effectively prevent the sudden failure of ESD grounding devices during work and essentially reduce the chances of ESD damages to the ESDS products during manufacturing or other sensitive operations.

In a traditional test, separate tests are usually applied to the footwear and the wrist strap. The test is inconvenient and time consuming, and many potential errors are generated, especially in the test of footwears. In testing the footwear, both feet of the user stand upon a single metal plate. If either one of the footwear passes the test, the test for footwear is then considered to pass the overall test. This is incorrect according to the international standards such as ANSI/ESD S20.20 or IEC-61340. This is because that it is impossible for a person to walk with both feet on the ground at the same time. In normal situation, one feet must be off the ground when a person walks. Once the footwear failing the test touches the ground, the person is not grounded transiently. During that short moment, the static electricity may be generated and harm the ESD-sensitive objects that a person may touch. All this is due to a defect in the footwear testing.

Using the traditional ways of wrist-strap and footwear testing, the test result is fuzzy and not precise so that the people under test can pass the test easily even some faulty results may occur in the test process. The test result is fuzzy because it is derived from resistance comparison with the high and low resistance limits without actual resistance calculation. The wrist strap and footwear are tested at separate times. Time is consumed and the operations are inconvenient.

Accordingly, the object of the present invention is to provide a method for testing personnel ESD grounding devices with a function of near-fail alert and a device for performing the same; in that a near-fail range is provided so that the user can receive an alert when the wrist straps or footwears worn on will fail soon in the near future and thus the user is reminded to take proper actions to change or fix the personnel ESD grounding device to prevent its sudden failure during actual use. Furthermore, the test provides digital readouts and has higher precision to avoid faulty results. Moreover, the wrist strap and footwear are tested simultaneously and individual results can be derived so as to avoid errors in test.

To achieve above object, the present invention provides a method for testing personnel ESD grounding devices with a function of near-fail alert; in that a near-fail range is set; when the measurement of the resistance of a wrist strap or a footwear is within the near-fail range; an alarm is actuated to alert the user that the static electricity prevention devices worn by the user will fail soon. The method further comprises the steps of: connecting the wrist-strap and/or footwear to be tested to the tester; pressing an actuating button to form a measuring voltage of each object to be tested; deriving a real voltage by operating the measured voltage with a reference voltage; deriving a value of resistance of the object to be tested by an operation to the real voltage; comparing the value of resistance with an upper limit and a lower limit for the object to be tested, wherein the upper limit and lower limit may be based on international standards such as ANSI/ESD S20.20; if the value of resistance is within a range between the upper limit and the lower limit, the object to be tested passes through the test and a pass indication to indicate the result is actuated; if the resistance value is out of a range between the upper limit and the lower limit, the object to be tested does not pass the test and a fail indication for indicating the result is actuated; and if the value of resistance has a difference from the upper limit or the lower limit within a predetermined range and is within the okay range between the upper limit and the lower limit; the value of resistance is at a range of near-fail, and a near-fail indication is actuated for alerting the user to replace the about-to-fail wrist-strap or footwear to prevent failure or to keep attention to such situation; and the predetermined range is settable as necessary by the user.

The present invention further provides a testing device for testing personnel ESD grounding wrist-strap or footwear with a function of near-fail alert. Basically the tester produces near-fail alarm in the following way: a near-fail range is set in the tester; when the measurement of the resistance for a wrist strap or a footwear is within the near-fail range; an alarm is actuated to alert the user that the static electricity prevention devices worn by the user will fail soon.

DETAILED DESCRIPTION OF THE INVENTION

In order that those skilled in the art can further understand the present invention, a description will be provided in the following in details. However, these descriptions and the appended drawings are only used to provide a clear means for those skilled in the art to understand the objects, features, and characteristics of the present invention, but not to be used to confine the scope and spirit of the present invention defined in the appended claims.

Figure 1:
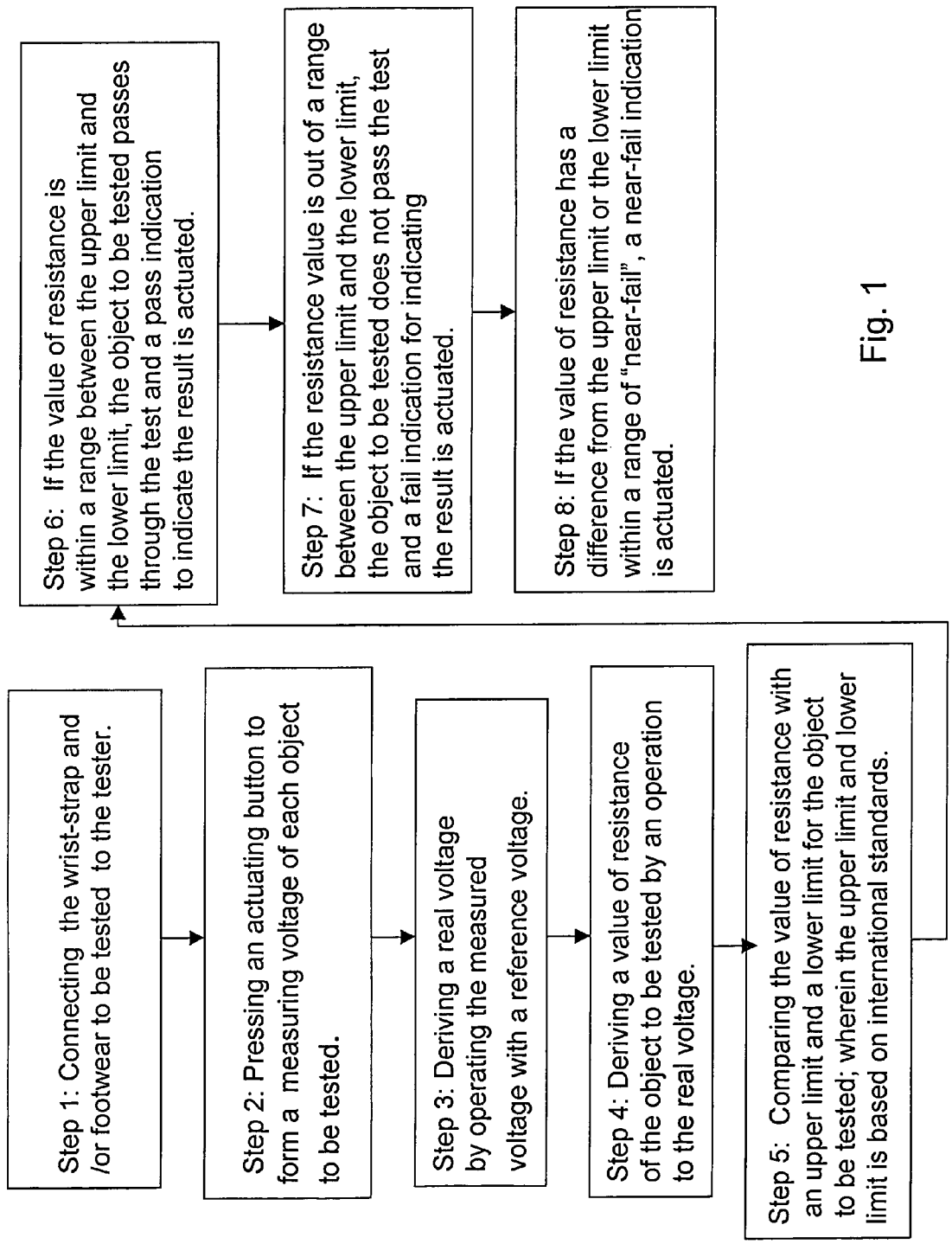
FIG. 1 shows the process of the present invention.
Figure 2:
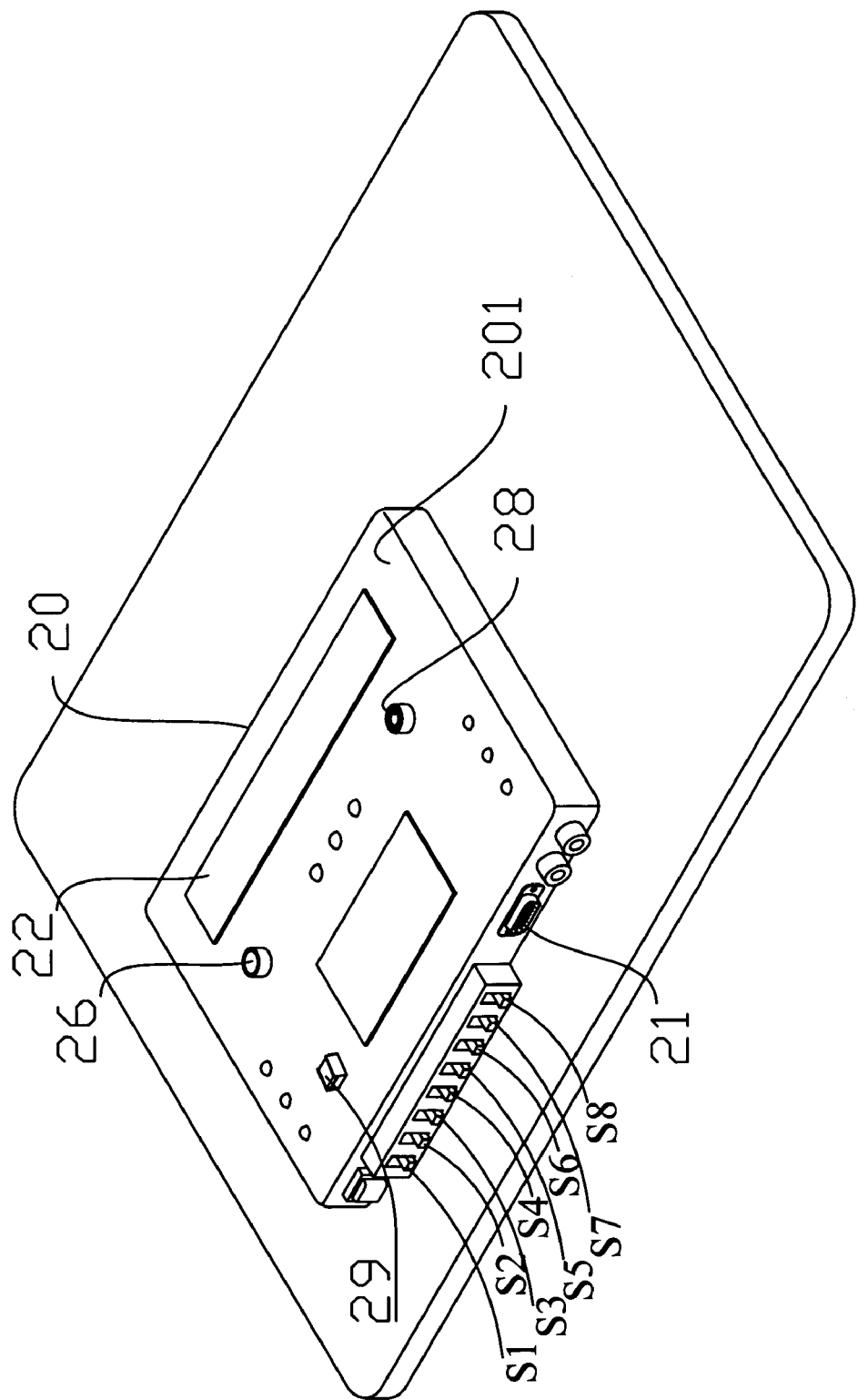
FIG. 2 shows the tester of the testing device of the present invention.

Referring to FIG. 1, the method and related structure of the present invention will be described herein.

The present invention provides a method for testing personnel ESD grounding devices with a function of near-fail alert. The method comprises the steps of:

1. Connecting the wrist-strap and/or footwear to be tested to the tester;
2. Pressing an actuating button to form a measuring voltage of each object to be tested;
3. Deriving a real voltage by operating the measured voltage with a reference voltage;
4. Deriving a value of resistance of the object to be tested by an operation to the real voltage;
5. Comparing the value of resistance with an upper limit and a lower limit for the object to be tested; wherein the upper limit and lower limit may be based on international standards such as ANSI/ESD S20.20.
6. If the value of resistance is within a range between the upper limit and the lower limit, the object to be tested passes through the test and a pass indication to indicate the result is actuated;
7. If the resistance value is out of a range between the upper limit and the lower limit, the object to be tested does not pass the test and a fail indication for indicating the result is actuated; and
8. If the value of resistance has a difference from the upper limit or the lower limit within a predetermined range and is within the okay range between the upper limit and the lower limit, we define that the value of resistance is at a range of "near-fail", and a near-fail indication is actuated for alerting the user to take proper reactions to such situation. In the present invention, the predetermined range is settable as necessary by the user.

Referring to FIGS. 2 to 6, a device for testing static electricity with a function of near-fail alert is illustrated. The object of the device is to test for normal functionality of the personnel ESD grounding devices and to provide the function of alert if any of the devices is about to fail. The near-fail alert is provided so that the user can take precaution to the failing state of the grounding devices so as to reduce the potential harms from static electricity.

The device of the present invention has the following elements.

A tester 20 is an approximate cubic casing. The lower surface of the tester 20 is attached to a holding plate 200. The tester 20 further includes the following elements (referring to FIG. 2).

A serial-transfer communication device 21 serves to support a serial-transfer communication instructions and can be connected to an external controller or computer for transferring test results thereto (such as a card reader for door access control or a computer), or receiving the instructions from an external controller. The tester has any kind of communication port, such as RS232, or USB, etc.

An LCD display 22 is located at an upper surface 201 of the tester and near the upper side of the surface 201 for displaying the test results in digits.

A plurality of LED (light emitting diode) alarm lights 24 serve for displaying testing results. Each set of LED alarm lights includes three lights of different colors including a red light, a yellow light and a green light.

In the test device of the present invention, the relation of the test resistance with the lights will be described herein.

(1) The yellow light shows that the value of resistance of the object under test is bigger than the upper limit. The test fails.
(2) The red light shows that the value of resistance of the object under test is smaller than the lower limit. The test fails.
(3) The green light shows that the value of resistance of the object under test is within the range between the upper limit and the lower limit and thus the test is a pass.
(4) If both the green light and the yellow light are actuated simultaneously, it represents that the resistance of the object to be tested is within a permissible range but it is also near the upper limit, that is, the object under test is near-fail high.
(5) If both the green light and the red light turn on simultaneously, it represents that the resistance of the object under test is within a permissible range but it is also near the lower limit, that is, the object under test is near-fail low.

Two plug-in holes for wrist straps with two different designs are provided, one plug-in hole 26 for traditional wrist straps and one plug-in hole 28 for dual-wire wrist straps. The two plug-in holes 26, 28 are arranged symmetrically at a left and a right side of the upper surface 201 of the tester.

The plug-in hole 26 serves for receiving traditional wrist strap for measuring the value of resistance on the loop formed by the wrist strap and the user's body. The other plug-in hole 28 serves to receive a special dual-wire wrist strap for deriving the resistance on the loop formed by each wire and the user's body in testing.

The push plate button 29 serves for actuating the testing process so that a central processing unit can activate other hardware devices in a pre-programmed procedure to measuree the resistance of the objects under test.

A plurality of DIP switches S1 to S8 (finger driving switches) are located at a front lateral side of the tester for selecting and controlling the test modes and upper and lower limits of resistance for the object under test.

The control functions performed through the DIP switches are described herein.

The DIP switch S1 serves for changing the lower limit of resistance of the wrist-strap and footwear between two international standards.

The DIP switch S2 serves for actuating the "OR" function about the testing of wrist-starp and footwear. In other words, when S2 is set, either wrist-strap or footwear passes the test, the overall test is treated as a pass.

The DIP switch S3 serves for setting the upper limit of the wrist straps.

The DIP switch S4 serves for enabling the test of wrist strap, otherwise, the wrist strap will not be tested.

The DIP switch S5 serves for setting the lower limit of the resistance value for the footwear.

The DIP switches S6 and S7 serve for setting the upper limit and the lower limit resistance value for the footwear.

The DIP switch S8 serves for enabling the test of the footwear, otherwise the footwear will not be tested.

Figure 3:
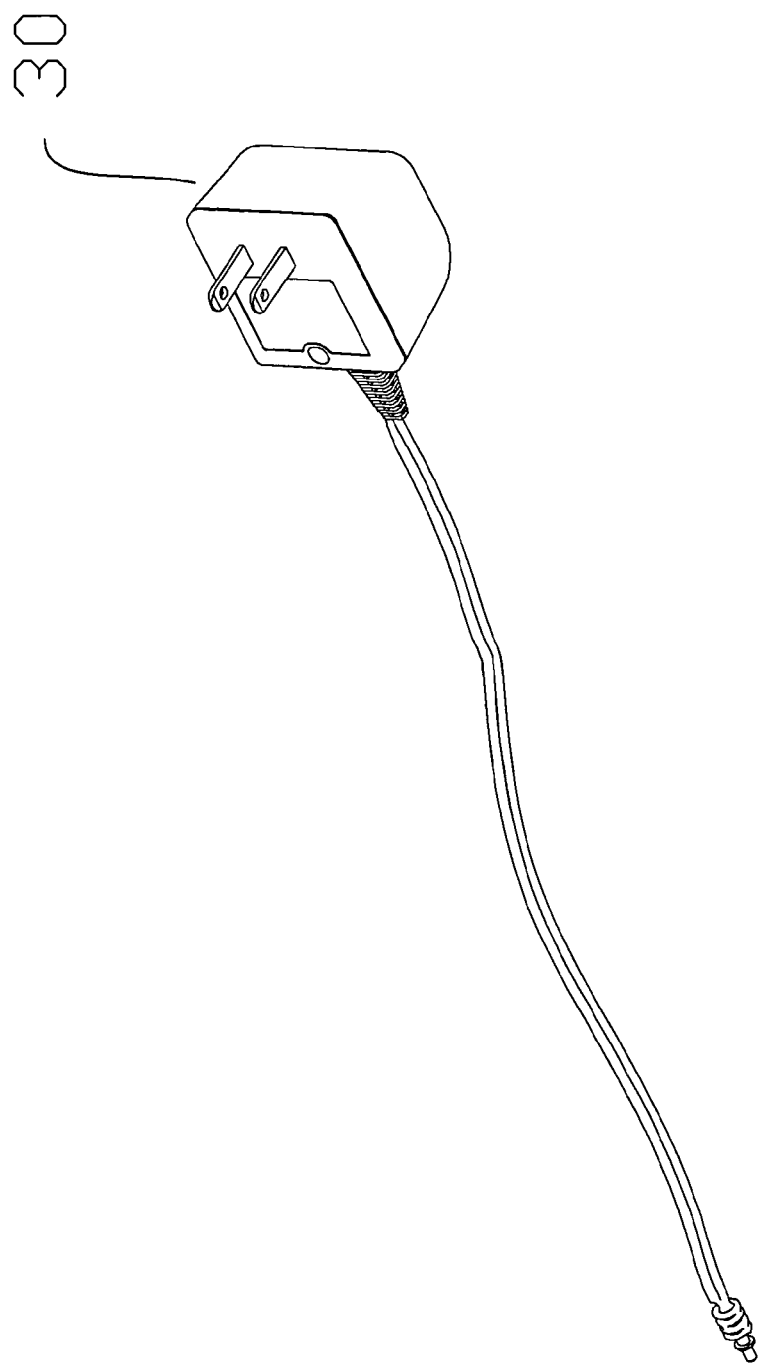
FIG. 3 shows the DC power supply of the testing device of the present invention.
Figure 4:
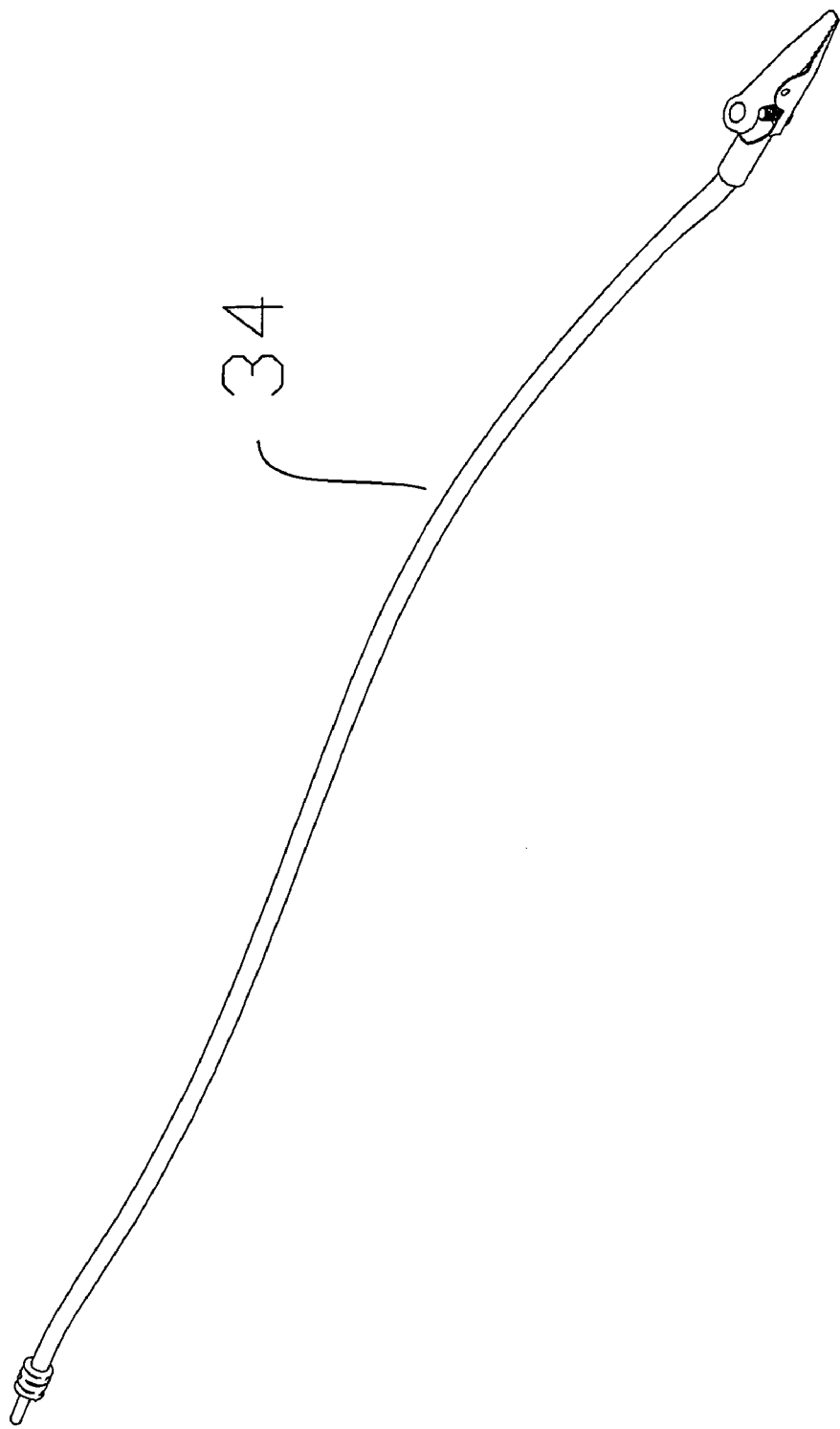
FIG. 4 shows a grounding wire of an RCA plug in the testing device of the present invention.

A DC power supply 30 serves for providing the DC power to the system of the present invention (referring to FIG. 3).

Figure 5:
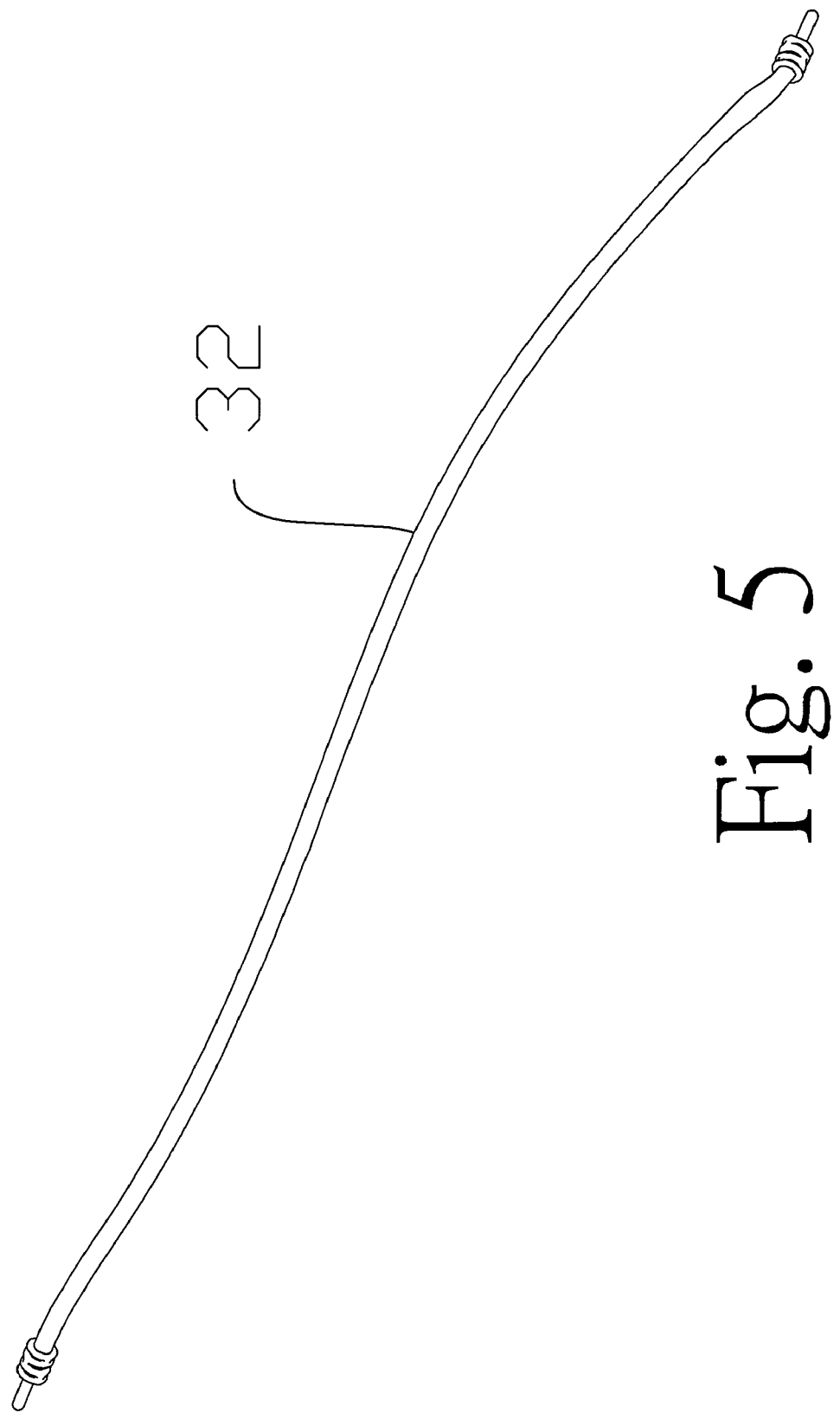
FIG. 5 shows the audio signal wire of the testing device of the present invention.

An audio signal wire 32 is connected between the tester and the footplate for signal transmission (referring to FIG. 5).

A plug-on grounding wire 34 has any form desired (such as an RCA plug). One end of the wire is connected to the tester for improving the stability in test (referring to FIG. 4).

Figure 6:
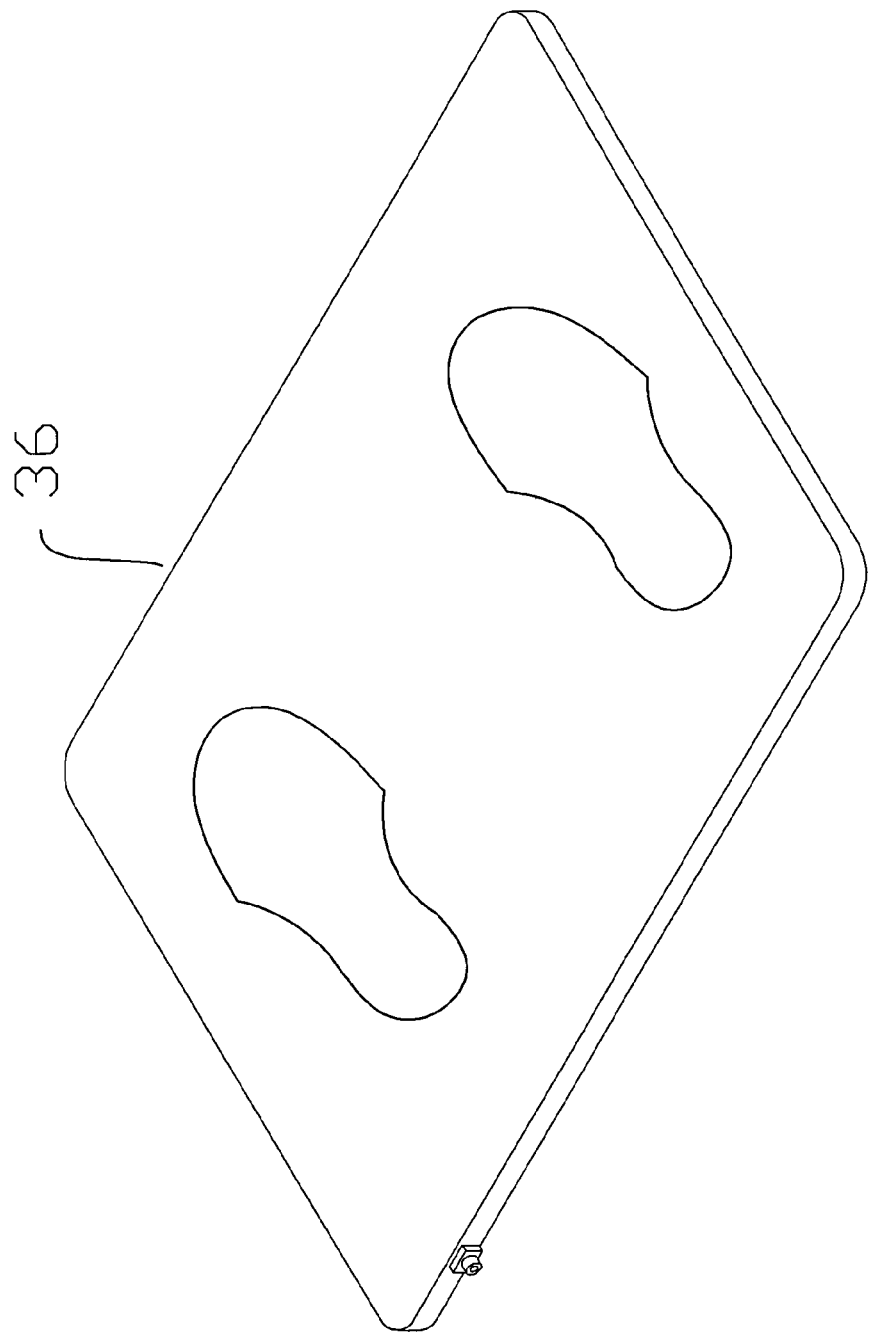
FIG. 6 shows the footplate in the testing device of the present invention.

The footplates 36 serve for connecting the two footwears back to the tester through the audio wire to form the two loops for resistance measuring (referring to FIG. 6).

The procedure to use the testing device includes the following steps:

1) Stepping on the footplate.
2) Inserting the wrist strap into the tester if the wrist strap is to be tested.
3) Pushing and hold the start-test button plate of the tester until the LCD and the LED alarm lights display the testing result.
4) Disconnecting the wrist-strap and stepping off the footplate.
5) If the test result is a pass, the test is completed. If the test result is a "NO-GO", check and correct the problem in the wrist-strap or the footwear and test again Moreover, the present invention provides a support for a paperless test, namely, the test result can be transferred out to a memory card, a computer or a flash (a portable memory disk) through the RS232 or the USB port.

The objective of the present invention is to provide a personnel ESD grounding devices tester with a function of displaying "near-fail" for alerting the user about the critical status of the wrist-strap or the footwear worn by the user. The novel features of the present invention are that: to enforce the person to perform the wrist-strap and footwear test; the value of resistance is displayed digitally; the near-fail alerts for the wrist-strap and footwear are provided; the value of resistance measured is transferred to an external controller (such as a door monitoring card reader or a computer) so as to have the effect of paperless testing and thus the record is trustable; the wrist-strap and the footwear can be tested simultaneously; the noises from human body are filtered effectively so as to have precise measurement results; the wrist-strap and the footwear are tested simultaneously so that the operation is convenient; and both of single wire wrist-strap and dual-wire wrist-strap can be tested by the device of the present invention; the left and the right foot can be tested independently and completely to meet the requirements specified in the international standards.

The present invention is suitable for many fields, such as SMT production lines, semiconductor clean-rooms; high-tech R&D rooms; national defense and military static electricity control areas; explosion control areas; aerospace maintenance and calibration areas; drug industries static electricity control areas; medical treatment areas; biochemical static electricity control areas, etc.

The present invention is thus described as above. The invention may be varied in other ways. Such variations are not to be regarded as a departure from the spirit and scope of the present invention, and all such modifications as would be obvious to one skilled in the art are intended to be included within the scope of the following claims.

What is claimed is:

1. A device for testing personnel ESD grounding devices with a function of near-fail alert; the device having a tester; wherein a near-fail range is set in the tester; when the measurement of the resistance for a wrist strap or a footwear is within the near- fail range; an alarm is actuated to alert a user that the static electricity prevention devices worn by the user will fail soon; and wherein the near-fail range is set in the test pass range, but near a test fail limit;

wherein the tester includes a plurality of LED alarm lights serve for displaying test results;

wherein each set of LED alarm lights includes three lights of different colors for displaying various test results;

wherein the lights includes a red light, a yellow light and a green light;

wherein the yellow light shows that the value of resistance of the object under test is bigger than the upper limit; and the test is a fail;

the red light shows that the value of resistance of the object under test is smaller than the lower limit; and the test is a fail;

the green light shows that the value of resistance of the object under test is allowable; and the test is a pass;

if both the green light and yellow light turn on simultaneously, it represents that the resistance of the object under test is within a permissible range but it is also near an upper limit, that is, the object under test is near-fail high; and if both the green light and red light turn on simultaneously, it represents that the resistance of the object under test is within a permissible range but it is also near a lower limit, that is, the object under test is near-fail low.

2. A device for testing personnel ESD grounding devices with a function of near-fail alert; the device having a tester; wherein a near-fail range is set in the tester; when the measurement of the resistance for a wrist strap or a footwear is within the near- fail range; an alarm is actuated to alert a user that the static electricity prevention devices worn by the user will fail soon; and wherein the near-fail range is set in the test pass range, but near a test fail limit; and wherein the tester further comprises a plurality of DIP switches for selecting and controlling the test modes and upper and lower limits of resistances for the object under test; and wherein the tester further comprises:

a DIP switch S1 for changing the lower limit resistance of the wrist-strap and footwear between two international standards;

a DIP switch S2 for actuating the "OR" function about the testing of wrist-strap and footwear; in other words, when S2 is set, either wrist-strap or footwear passes the test, the overall test is treated as a pass;

a DIP switch S3 for setting the upper limit of the wrist straps.

a DIP switch S4 for enabling the test of wrist strap, otherwise, the wrist strap will not be tested;

a DIP switch S5 for setting the lower limit of the resistance value for the footwear;

a DIP switches S6 and S7 for setting the upper limit and the lower limit resistance value for the footwear;

a DIP switch S8 for enabling the test of the footwear, otherwise the footwear will not be tested.

3. A device for testing personnel ESD grounding devices with a function of near-fail alert; the device having a tester; wherein a near-fail range is set in the tester; when the measurement of the resistance for a wrist strap or a footwear is within the near-fail range; an alarm is actuated to alert a user that the static electricity prevention devices worn by the user will fail soon; and wherein the near-fail range is set in the test pass range, but near a test fail limit; and wherein the tester further comprises:

a DC power supply for providing DC power to the system of the present invention;

an audio signal wire connected between the tester and a footplate for signal transmission;

a plug-in grounding wire; one end of the wire being connected to the tester for improving the stability in test; and a footplate for connecting the two footwears back to the tester through the audio wire to form the two loops for resistance measuring.

\* \* \* \* \*